United States Patent [19]

Kubiatowicz et al.

[11] 4,208,398
[45] Jun. 17, 1980

[54] TECHNETIUM-LABELED COMPLEXES, PRODUCTION AND USE THEREOF

[75] Inventors: David O. Kubiatowicz, Arden Hills; Theodore F. Bolles, Woodbury, both of Minn.

[73] Assignee: Hoffman-La Roche Inc., Nutley, N.J.

[21] Appl. No.: 570,254

[22] Filed: Apr. 21, 1975

Related U.S. Application Data

[63] Continuation-in-part of Ser. No. 353,298, Apr. 23, 1973, abandoned.

[51] Int. Cl.² ............... A61K 29/00; A61K 43/00
[52] U.S. Cl. .................... 424/1; 260/429.1; 424/9
[58] Field of Search .................................. 424/9

[56] References Cited

U.S. PATENT DOCUMENTS

| | | | |
|---|---|---|---|
| 3,873,680 | 3/1975 | Jackson et al. | 424/1 |
| 3,928,552 | 12/1975 | Winchell et al. | 424/1 |

*Primary Examiner*—Benjamin R. Padgett
*Assistant Examiner*—Christine M. Nucker
*Attorney, Agent, or Firm*—Jon S. Saxe; Bernard S. Leon; William H. Epstein

[57] ABSTRACT

Novel chemical complexes containing a radioactive technetium isotope are kidney specific when the complexing agents are certain ionic, water-soluble mercaptans. The complexes can be made by reducing pertechnetate ion and reacting the reduced technetium species with the mercaptan. The complexes are normally used in a biologically sterile, substantially isotonic aqueous medium, for diagnostic purposes.

13 Claims, No Drawings

TECHNETIUM-LABELED COMPLEXES, PRODUCTION AND USE THEREOF

RELATED APPLICATIONS

This application is a continuation-in-part of our co-pending application Ser. No. 353,298, filed Apr. 23, 1973, abandoned.

FIELD OF THE INVENTION

This invention relates to chemical complexes of the radioactive, metastable isotope technetium-99m (Tc-99m) wherein the complexing agents are selected from certain water-soluble mercaptans. A further aspect of this invention relates to a process for producing the chemical complex and a preferred biologically sterile, substantially isotonic medium containing the complex. Still another aspect of this invention relates to the use of the products of the invention in studies of kidney structure and function.

DESCRIPTION OF THE PRIOR ART

The art of radiochemistry has found many applications in the fields of medicine and biology. It has long been known that the introduction into an organism of compounds containing (or "labeled" with) a radioisotope can provide insight into the anatomy and physiology of the organism. These compounds, generally referred to as radiopharmaceuticals, are particularly useful in diagnostic techniques which involve studying the structure or function of various internal organs, e.g. the kidney, with radiation detection means. For diagnostic work, isotopes with a short half-life and an emission spectrum rich in gamma rays (as opposed to beta particles) are preferred.

The metastable isotope Tc-99m has a six hour half-life and an emission spectrum, 99 percent gamma radiation at 140 KeV, which is extremely well-suited for techniques of diagnostic nuclear medicine. Thus, Tc-99m has a high specific activity, $5.28 \times 10^9$ millicuries per gram (mCi/g), and a conveniently rapid rate of decay; whereas its daughter product, Tc-99, has a specific activity which is almost nine orders of magnitude lower and a half-life which is roughly eight orders of magnitude longer. For the organism being studied or diagnosed, the slow rate of decay from the relatively stable, lower specific activity Tc-99 to its degradation product (ruthenium) would not normally produce any hazardous amounts of radiation, regardless of the biological means or route of elimination of a Tc-99m radiopharmaceutical. For the researcher or clinician, the emission spectrum of Tc-99m can provide high levels of accuracy in radiodiagnostic measurements and calculations. In recent years, Tc-99m has become readily available in hospitals through the use of selective elution from a so-called molybdenum-99 (Mo-99) generator. The isotope Mo-99 produces Tc-99m as a radioactive decay product.

Although Tc-99m compounds would appear to be ideal radiopharmaceuticals for diagnostic use, providing or selecting Tc compounds or complexes with a view toward organ specificity and tolerable levels of toxicity is not a simple matter of selection. Obviously, compounds with a very high toxicity are undesirable for human or veterinary use, even in the small amounts called for by diagnostic work. Compounds with insufficient in vivo stability may be poor diagnostic tools, since radioactive ions or other chemical species with insufficient or undesired organ specificity may be liberated. Stable compounds which become distributed generally throughout the organism, despite their stability, or which do not reach a desired destination in the organism are also poorly suited for many studies of organ function or structure, e.g. kidney studies.

The problem of selecting or preparing a kidney specific radiopharmaceutical for kidney imaging or function studies is particularly difficult. Both the liver and the kidney are capable of removing various types of compounds from the body—ultimately through excretion in feces and urine, respectively. Any radiopharmaceutical used for kidney studies should ideally have maximal kidney specificity and minimal liver specificity. A number of biological and chemical factors must be considered and brought under control before the desired organ specificity and route of excretion can be obtained.

For the study of kidney structure, for example, Tc-99m-containing agents are preferably more slowly cleared, or even quantitatively absorbed and retrieved by kidney tissue, so as to permit visualization of kidney structure by scanning instruments. An example of a useful agent of this type is $^{99m}$Tc-dimercapto succinic acid. Under certain circumstances, however, as where modern high-speed gamma cameras are available, kidney structure can be studied using technetium compounds which are rapidly cleared from kidney tissue such as thiosaccharide $^{99m}$Tc-thioglucose and $^{99m}$Tc-mercapto succinic acid as disclosed herein.

Technetium-99m compounds have been used in brain or other organ scanning. For example, Tc-sulfur colloid can be used for liver scanning.

Representative of the literature relating to the radiopharmacology of Tc-99m compounds are the following articles:

Larson et al, J. Nuclear Medicine, 7:8:7 (1966) relating to Tc-99m-colloid preparation for photo-scanning, lung imaging and pancreas imaging;

Tubis et al, International Journal of Applied Radiation and Isotopes, V. 19, 835 (1968), relating to Tc-99m-labeled cystine, methionine, and a synthetic polypeptide and their distribution in mice; and U.S. Pat. No. 3,466,361, showing preparation of chelates of technetium and their use for various diagnostic purposes.

Compared to the common transition metals, very little is known about the chemistry of technetium. Technetium belongs to Group VII-B of the Periodic Table; its chemistry bears a superficial resemblance to manganese but tends to be more similar to the higher member of the Group, rhenium. Technetium can apparently exist in a range of oxidation states, including +7 (e.g. pertechnetate) and several lower oxidation states, some of which are difficult to characterize and/or are relatively unstable. In spectrophotometric determinations of technetium, the element has been complexed with toluene-3,4-dithiol, thioglycolic acid and thiocyanates. See Miller et al, Anal. Chem., page 404 (1961) and page 1429 (Oct. 1960), and Crouthamel, Anal. Chem., page 1756 (Dec. 1957).

The complexes of the present invention must not, however, be confused with the colored complexes used for analysis as described in these references. The analytical procedures use colorimetric techniques. It seems clear that these are formed using far higher concentrations of technetium than those used in the present invention; and it is believed that the colored substances and solutions used for analytical purposes for determination of technetium do not suggest the present pharmaceutically acceptable nor their unique biological behavior or use for the diagnostic methods described herein.

Accordingly, this invention contemplates providing pharmaceutically acceptable complexes of Tc-99m which have sufficient in vivo stability and sufficiently low toxicity for use in humans or animals and which preferably are:

Removed from the blood or other vital organs or tissues by the kidney rather than by, for example, the liver or the lungs;

Concentrated in the kidney at a high rate if visualization is desired;

Concentrated in other organs or tissues—particularly organs or tissues in close proximity to the kidney—at a very low or negligible rate;

Eliminated from the body by alternative routes to a minor, preferably negligible, extent.

This invention further contemplates means and methods whereby Tc complexes can be most efficiently produced and utilized for kidney structure studies.

BRIEF SUMMARY OF THE INVENTION

Briefly, this invention involves reducing an appropriate amount of radioactive pertechnetate ion ($^{99m}TcO_4^-$) until a major amount of the pertechnetate ion has been reduced to a technetium species having an oxidation state greater than 0 but less than +7 and then reacting this technetium species with an excess of one of the subsequently described sulfur-containing complexing agents. The resulting Tc-99m complex is suitable for injection into the blood stream of a mammal when dissolved or dispersed in a biologically sterile, aqueous medium substantially isotonic with mammalian body fluids. The reduction step can be carried out chemically through acid catalysts if the complexing agent is also a reducing agent, at least when the complexing agent is present in large excess, as will normally be the case. Preferably, however, reduction is achieved through an iron (II) salt, a copper (I)/copper (II) couple, a tin (II) salt, or a combination of two or more of these agents.

A meaningful evaluation of kidney function can be obtained by measuring the increase in and loss of radioactivity from the kidney of the animal or patient being studied. It will generally not be necessary to monitor the radioactivity for more than about 24 hours after the injection, and 12 hours of monitoring can be fully sufficient.

Kidney structure can be determined by gamma radiation detectors to measure and record the radioactivity emitted from the kidney.

The complexing agents useful for the purpose of the invention are thiol-group-containing, pharmaceutically acceptable, water-soluble organic acids having from 2 to 15 carbon atoms. In addition to the thiol group they contain as acidic moieties hydroxyl, carboxylic or sulfonic groups.

They also exhibit certain oil-water partition behavior.

DETAILED DESCRIPTION OF THE INVENTION

The complexing agents of the invention are organic thiols which are capable of providing a kidney-specific, radioactive technetium-containing compound suitable for inclusion in injectable media substantially isotonic with mammalian body fluids. These compounds are rapidly removed from the blood or other tissues by the kidney, are present in the kidney for a time and then excreted by the kidney into the bladder, and therefore removed from the body more or less completely by way of the urine. Thus, the selection of complexing agents according to this invention involves weighing a combination of chemical and biological criteria. Chemical consideration of the complexing agent alone does not insure that the technetium complex will have a kidney specificity, compatibility with blood or other mammalian body fluids, or the like.

The compounds useful as complexing agents for technetium, which are to be used as diagnostic agents for kidney structure and function are water-soluble and stable at the pH of the blood, namely about pH 7.4. In every case they contain a mercaptol or thiol, i.e. -SH group, which is the site of complexing with the Tc-99m.

Broadly speaking, the complexing agents of the invention are aliphatic thiol compounds and certain thiosaccharides having from 2 to 15 carbon atoms, to which are attached, as substituents, one or two thiol groups, together with from one to five acidic functional groups of the class consisting of hydroxyl, carboxylic or sulfonic groups, not more than three carboxylic groups or one sulfonic group being present. In every case there is at least one of the described functional groups present for every three carbon atoms in the compound. The aliphatic carbon chains which are present are straight or branched.

The complexes of the invention are soluble to the extent of about 0.01 percent to 100 percent by weight in water. A useful test to determine whether the complexes are useful for the purposes of the invention is the determination of the partition coefficient of the complex between water and octanol (hydrophilicity). This ratio of distribution is quite easily followed by determining the activity of the respective phases of a two-phase system, in which the complex is added as a water solution to octanol in equal parts. In this system, complexes useful for the purposes of the invention show the following relationship $$Ln \frac{a_w}{a_o} \geq 2$$

(wherein $a_w$ is the radioactivity distributed in the aqueous phase and $a_o$ is the radioactivity distributed in the organic phase, at a pH in the range between pH 4 and pH 9), after thorough agitation to admix the phases followed by standing to accomplish complete separation. Further, the partition coefficient is relatively uniform throughout the stated pH range; i.e., does not change more than about three units over this range.

The following table illustrates the water/octanol partition coefficient for Tc-99m-dimercaptosuccinic acid in a concentration of 0.027 mole/liter:

TABLE I

| pH | Partition Coefficient = $Ln(a_w/a_o)$ |
|---|---|
| 4 | 6.0 |
| 5 | 6.8 |
| 6 | 7.6 |
| 7 | 8.5 |
| 8 | 8.2 |
| 9 | 8.1 |

In addition, the Tc-99m complexes of the invention, when chromatographed on unactivated, 100-micrometer thick silica gel sheet with polyvinyl alcohol binder at neutral pH, and developed with anhydrous acetone, are not desorbed, i.e. show Rf=0, whereas unreacted aqueous pertechnetate shows Rf=1.0. However, when developed with anhydrous acetone:concentrated HCl in a volume/volume ratio of 100:0.5, the complexes of the invention show Rf=about 0.6.

Typical of the compounds useful for forming the complexes with Tc-99m are dimercaptosuccinic acid, dimercapto glutaric acid, dimercapto adipic acid, mercaptosuccinic acid, mercaptoacetic acid, mercaptopropionic acid, 3-mercaptopropylsulfonic acid, thioglucose and thiolactic acid.

The term "substantially isotonic with mammalian body fluids", as used herein, denotes the condition when the osmotic pressure exerted by the solution in question is sufficiently similar, as compared to a body fluid such as blood, so that no dangerous hypo- or hypertonic condition results in the patient or test animal when 0.1 ml. (in the case of a mouse) or up to 10 ml. (in the case of a human) of the solution is injected into the patient's or animal's bloodstream.

The exact mechanism by which the complexing agents used in this invention become chemically linked to technetium is difficult to determine. It appears that the Tc-99m should be present primarily in an oxidation state of at least about $+3$ but not more than $+6$. This oxidation state can be conveniently obtained by reducing Tc-99m-pertechnetate, a relatively stable $+7$ technetium species. The reduced species can coordinate with one or more sulfur atoms which are in the form of mercaptan groups.

The amount of Tc-99m needed to produce an amount of radiopharmaceutical suitable for most diagnostic or research uses is extremely small and is generally in the range of about 0.01 millicurie per milliliter (mCi/ml) of 99m-pertechnetate solution up to about 500 mCi per ml. of such solution. Only about $0.02 \times 10^{-10}$ gram of 99m-pertechnetate dissolved in a milliliter of aqueous medium (e.g. isotonic saline) is needed to provide 0.01 mCi/ml, and less than $100 \times 10^{-10}$ gram of 99m-pertechnetate per milliliter of solution provides enough radioactivity for most uses.

Owing to the short half-life of the Tc-99m, it is preferred to prepare small batches of 99m-pertechnetate solution for immediate use. Batches as small as 0.1 ml. can be adequate for animal studies (e.g. for injection in mice), and batches as large as 50 ml. are convenient for one or more injections in one or a group of human patients. In any event, it would be a rare situation that required more than about $100 \times 10^{-10}$ gram (i.e. about $10^{-10}$ gram-atoms) of Tc-99m as pertechnetate ion to produce a few ml. of radiopharmaceutical, regardless of stoichiometry of the Tc complex. It is preferred to provide enough complexing agent (ordinarily at least $5 \times 10^{-9}$ moles per milliliter of reaction mixture) to have an excess over stoichiometry with respect to the Tc-99m in the reaction mixture. A large excess of complexing agent (e.g. 0.5–1000 micromoles of complexing agent per ml. of reaction mixture) can be desirable, particularly when the complexing agent itself serves as the means for reducing the oxidation state of pertechnetate.

The Tc-99m used in this invention is obtainable from a Mo-99 generator in the conventional manner. Eluting or "milking" the generator with an aqueous medium will provide the Tc-99m-pertechnetate solution in the form of $M^{+x}(99m\text{-}TcO_4^-)_x$, where $M^{+x}$ is a pharmaceutically acceptable cation such as a proton, an alkali metal ion, an ammonium ion or the like, and x is a positive integer less than four. Typically, the aqueous elution medium is a saline solution, which provides sodium 99m-pertechnetate.

The pertechnetate ion can be reduced chemically or electrolytically to a lower oxidation state of technetium, preferably by reaction with an oxidizable low valence metal salt such as a tin (II) salt (e.g. $SnCl_2$), an iron (II) salt (e.g. a ferrous salt/ascorbic acid medium), a Cu(I)/Cu(II) couple, a combination thereof, or other chemical reducing agents such as mercaptans, metal hydrides, thiosulfates, hypophosphites, bromides, iodides, etc.

To avoid possible accidental contamination of the complex with undesirable metal ions, the preparation steps are carried out in glass vessels, and the use of hypodermic needles for transferring solutions of the mercaptan compounds is avoided.

A particularly suitable means for providing the reducing agent and complexing agent is to pre-formulate a radiopharmaceutical kit for use with the No-99 generator. For example, 0.1 (preferably at least 0.5) to 10 ml. of a solution containing about 0.5 to about 1000 micromole/ml. of complexing agent and a suitable amount, e.g. 0.01–100 micromole ml. of reducing agent can be hermetically and aseptically sealed in separate vials or the same vial. The contents of the vial or vials can further be treated (for example by freeze drying) to produce a dry powder. A preservative such as benzyl alcohol is optionally included in the contents of the vial. The solution in the vial or an aqueous solution of the dry powder is preferably substantially isotonic with mammalian body fluids, e.g. human blood. The contents of the vial can be combined with the pertechnetate-containing, substantially isotonic eluate, mild heat can be applied if necessary to the combined solutions to achieve the reduction and Tc-complex formation, and the resulting radiopharmaceutical can then be injected into the blood of the patient or test animal.

Conveniently, the container is provided with a plunger means and means for attaching a hypodermic needle so that the vial functions as a hypodermic syringe, whereby the contents after preparation of the solution of Tc-99m complex can be injected parenterally without being transferred to another container or syringe.

Radioactivity measurements are made in the conventional manner for a period from the time of injection until about 24 hours afterwards, depending on the nature of the study or diagnosis. Most studies call for at least one-half hour of post-injection radioactive measurements. These measurements can be corrected for decay in the usual manner and studied with a view toward obtaining a picture of kidney structure or a measure of kidney function.

The amount of complexing agent injected into a test animal or human patient should preferably be less than 25 percent (e.g. less than 10 percent) of the LD 50 in mg. per kg. of body weight, though higher amounts are permissible in veterinary medicine. Typical LD 50's (determined in rodents and at least one other species) for preferred complexing agents of this invention range from about 20 to 1000 mg. per kg. of body weight.

When optical isomerism is possible, as in the case of dimercaptosuccinic acid, DL-racemic mixtures are fully operative in the invention and are easier to synthesize than the individual isomers. If desired, however, racemic mixtures can be resolved by conventional techniques.

Acid, salt or hydroxyl groups present on the complexing agent molecule can provide a water-solubilizing or hydrophilic effect which is reflected in higher $L_n(a_w/a_o)$ values, but due regard must be accorded to the variety of fluids, organs and tissues in mammals, each of which can have a distinctively acidic or basic environment, ranging from, for example, the low pH of the stomach to the relatively high pH of the intestines. The blood is on the mildly alkaline side at pH=7.4, while the urine, etc., is about pH 5 to pH 8. Thus, partition coefficient data on the Tc-complexes of this invention are preferably obtained throughout the pH range of 4 to 9. The use of partition coefficient data in pharmacology is well-established; see Andrejus Korolkvas, Essentials of Molecular Pharmacology, Wiley (Interscience), New York (1970). It has now been found that the water/n-octanol system provides useful data for evaluating lipophilic-hydrophilic balance of Tc-complexes without in vivo testing. Natural logarithms of partition coefficients are tabulated in several of the examples which follow.

Due regard should also be given to chelating effects of the water-solubilizing groups COOH, $SO_3H$ and OH.

In the preparation of the complexes, when the complexing agents of this invention are used together with an oxidizable lower valence metal salt, the salt can be combined with a water solution of the complexing agent. For example, mercaptosuccinic acid can be dissolved in a sodium bicarbonate-water solution, and a reducing agent comprising an excess over stoichiometry of $$SnCl_2 \cdot 2H_2O$$

dissolved in ethanol or 1 molar aqueous HCl can then be added to the solution. After the complexing and reducing agents have been combined, 99m sodium pertechnetate can be added. Agitation at a normal ambient temperature (20°–25° C.) will initiate the reduction step, and over 50 percent (in practice more than 80 percent) of the pertechnetate ion will be in reduced form after less than an hour at this ambient temperature. The extent of reduction can be determined with thin layer chromatography (T.L.C.) and radiation monitoring, since $TcO_4^-$ and its reduced-and-complexed form have distinctly different $R_f$ values if the chromatogram is developed with properly selected solvents.

If the oxidizable low valence metal salt is omitted, the sodium pertechnetate eluate can be reacted with HBr to form $H_2{}^{99m}TcBr_6$. This reaction is preferably carried out by repeatedly evaporating the eluate in the presence of 0.1 N (or more concentrated) aqueous HBr under an atmosphere of dry, inert gas such as nitrogen. The $H_2TcBr_6$ can be extracted with acetone, reacted with an excess of the mercaptan complexing agent in a nonaqueous medium to form the Tc complex, and then worked up in saline solution or the like. Further pH changes can be used, if necessary, to dissolve the Tc complex.

The amount of radioactive $^{99m}Tc$ required for use in imaging is relatively very small, being of the order of 1 to 100 millicuries of $^{99m}Tc$ per mg. of complexing agent. A total amount of 2 millicuries of radioactive material typically suffices for test purposes in the average (70 kg.) human.

It is much more convenient to measure out larger amounts of complexing agent than that which is just sufficient to complex with the very small amount of radioactive material. Any residual acidic function of the complexing agent is conveniently neutralized using a solution of sodium hydroxide or sodium bicarbonate. The tonicity of the agent is adjusted to substantially isotonic with sodium chloride, if necessary. The substantially isotonic radiopharmaceutical is then ready for injection.

The distinct $R_f$ values of novel Tc-mercaptan compounds or complexes produced according to this invention can reliably characterize these compounds so that they are distinguished from their precursors. Since only minute amounts of complexes of Tc-99m are produced, analysis of the complex by any method other than T.L.C. is extremely difficult at best. To reproducibly determine the $R_f$ values, thin layer chromatographs can be made from appropriate solutions and a standardized chromatogram sheet. Reproducible results have been obtained with unactivated, 100 micron thick silica gel chromatogram sheets having a polyvinyl alcohol binder and a neutral pH. One commercially available form of such a chromatogram is designated Eastman Chromagram Sheet 6060.

EXAMPLE 1

Preparation of the Kidney Specific, Technetium Complex with Dimercaptosuccinic Acid About 5 millicuries of 99m-$TcO_4$ ($10^{-9}$ gms.) in 2 ml. of saline solution (as an eluate from a Mo-99-Tc-99m generator) were placed in a 10 ml. glass vial. Two ml. of 48 percent aqueous HBr were added to the vial, and the vial contents were evaporated to dryness over a steam bath under a $N_2$ atmosphere. This evaporation procedure was repeated twice, resulting in the formation of $TcBr_6{}^{-2}$.

Ten milligrams of dimercaptosuccinic acid (DMSA) in about 3 ml. of absolute ethanol were added to the $TcBr_6{}^{-2}$ residue in the vial. The alcoholic solution was evaporated to about 0.5 ml. volume.

Next, 9 ml. of saline were added to the glass vial (held under $N_2$ atmosphere). The pH of the vial contents was raised to pH 7.4, using 1 molar NaOH. The solution was transferred to a pharmaceutical vial, capped and sealed. Using a needle inserted through the rubber seal septum, the vial was evacuated to 5 mm. Hg pressure and purged with nitrogen to 1 atmospheric pressure. The vial contents were ready for injection and kidney imaging. Good kidney images in dogs were obtained one-half hour after injection of this solution, using a gamma radiation detecting camera.

Table II shows the distribution of 99mTc-DMSA in white female Swiss Webster mice, each weighing about 20 grams. The mice were injected intravenously via the tail vein, sacrificed after appropriate time periods, then dissected. The isolated organs were assayed for radioactivity using a Packard series 410 A Auto Gamma Spectrometer. Percent activity distribution was calculated (allowance was made for the radioactive decay of Tc-99m) and is shown in the table.

TABLE II

Biological distribution of 99m-Tc-dimercaptosuccinic acid in mice as a function of time
Percentage of total 99m-Tc in mice as a function of time

| Organ | 0 hr. | 0.5 hr. | 1.0 hr. | 2.0 hr. | 4.0 hr. | 24.0 hr. |
|---|---|---|---|---|---|---|
| Lungs | 7.4 | 2.3 | 1.7 | 0.8 | 0.7 | 0.0 |
| Liver | 28.6 | 12.8 | 9.4 | 6.8 | 3.8 | 2.7 |
| Spleen | 0.3 | 0.4 | 0.2 | 0.3 | 0.1 | 0.1 |
| Kidneys | 9.4 | 29.3 | 39.5 | 45.6 | 54.8 | 75.5 |
| Stomach | 1.8 | 1.1 | 1.2 | 0.5 | 0.4 | 0.4 |
| Gut | 10.1 | 6.1 | 7.0 | 4.3 | 3.0 | 1.7 |
| Pancreas | 1.4 | 0.7 | 0.4 | 0.3 | 0.2 | 0.2 |
| Carcass | 40.9 | 30.4 | 26.9 | 20.4 | 21.3 | 8.0 |

Each data point represents an average value from three mice taken in three separate distribution studies.

Activity begins to accumulate in the animal's kidneys immediately after injection of the Tc-DMSA complex and continues to concentrate during a 24 hour period. These data can be compared to mouse kidney distribution data of Tc-99m pertechnetate, which concentrates to a maximum of 3 percent at any time during a 24 hour period.

Thin layer chromatographic analysis of the Tc-DMSA complex was performed as follows:

Chromatogram: Unactivated 100-micrometer thick silica gel sheet with polyvinyl alcohol binder, neutral pH (Eastman Chromagram 6060).

Solvent Systems: (1) anhydrous acetone; (2) anhydrous acetone-concentrated aqueous HCl (36 percent) in a volume/volume ratio of 100:5.

Developed Chromatograms: Tc-DMSA developed with (1), Rf=0, whereas unreacted pertechnetate had an Rf=1.0. Tc-DMSA developed with (2), Rf=0.63, whereas unreacted pertechnetate had an Rf=1.0.

EXAMPLE 2

Preparation of Technetium Dimercaptosuccinic Acid for Kidney Imaging using Mercaptan Reduction in HCl.

Twenty-five mg. of dimercaptosuccinic acid were added to a 20 ml. pharmaceutical vial containing 1 millicurie of 99m-TcO$_4$$^-$ in 4 milliliters of 0.5 molar HCl. The vial was closed, vented with a hypodermic needle, and placed in a boiling water bath for 10 minutes.

One molar NaOH was added to the cooled vial until the pH of the solution was raised to 7.6. The vial was evacuated and purged with N$_2$. The solution of dimercaptosuccinic acid complex was then ready for injection.

EXAMPLE 3

Preparation of Kidney Specific Agent Technetium-thioglucose

About 1 millicurie of 99m-TcO$_4$$^-$ in 0.2 milliliter of saline solution was added to a glass vial. Two milliliters of 48 percent HBr were added to the vial, and the vial contents were evaporated to dryness over a steam bath under a N$_2$ atmosphere. The evaporation procedure was repeated twice.

The residue of 99m-TcBr$_6$$^-$ was dissolved by adding two milliliters of ethanol. Twenty-five milligrams of sodium thioglucose were added, and the solution was evaporated to near dryness using a stream of warm N$_2$.

Ten milliliters of saline solution were added to dissolve the 99m-Tc-thioglucose complex. The solution pH was 7.4.

Thin layer chromatographic analysis of the Tc-thioglucose complex was performed as described in Example 1. The results were:

Tc-thioglucose developed with (1), Rf=0. Unreacted pertechnetate had an Rf=1.0. Tc-thioglucose developed with (2), Rf=0.63 and 0.75.

Table III shows the distribution of 99m-Tc-thioglucose in female white Swiss Webster mice. The mice were tested and assayed for radioactivity as described in Example 1.

TABLE III

Biological distribution of 99m-Tc-thioglucose in mice as a function of time.
Percentage of total 99m-Tc in mice as a function of time.

| Organ | 0 hr. | 0.5 hr. | 1 hr. |
|---|---|---|---|
| Lungs | 2.9 | 0.3 | 0.08 |
| Liver | 18.9 | 2.1 | 3.3 |
| Spleen & Pancreas | 2.1 | 0.1 | 0.2 |
| Kidneys | 9.0 | 2.8 | 0.4 |
| Stomach | 0.8 | 0.8 | 0.06 |
| Gut | 13.3 | 5.5 | 1.1 |
| Carcass | 53.1 | 1.5 | 1.4 |
| Urine | 0.0 | 89.9 | 93.5 |

This compound is eliminated from the kidneys of the mice very rapidly as shown by the percentages of technetium activity found in the various organs during the test time periods. The "0 hr." test data do not indicate compound specificity but rather blood flow to various organs.

Technetium-thioglucose can be used for kidney imaging when a gamma camera is employed, or it can provide a measure of kidney function by monitoring its disappearance from the animal's bloodstream.

EXAMPLE 4

Preparation of Kidney Specific Agent Technetium-mercaptoacetic Acid

About 3 millicuries of 99m-TcO$_4$$^-$ were added to a glass vial. One milliliter of 48 percent HBr was added to the vial, and the vial contents were evaporated to dryness over a steam bath under a N$_2$ atmosphere. The evaporation procedure was repeated twice.

Twelve milligrams of mercaptoacetic acid dissolved in 4 milliliters of acetone were added to the dry 99m-TcBr$_6$$^=$ residue. After 20 minutes the acetone solution was evaporated to near dryness, then dissolved with 5 milliliters of saline solution. 0.5 Percent of sodium hydroxide solution was added to adjust the solution pH to 7.4.

One hour after this complex was injected into the blood stream of a mouse, about 24 percent of technetium activity had localized in its kidneys. A large part of the remaining activity was found in the animal's urine.

The partition coefficient Ln(a$_w$/a$_o$) for technetium-mercaptoacetic acid is shown in the following table:

TABLE IV

| Solution pH | Partition Coefficient - Ln(a$_w$/a$_o$) |
|---|---|
| 4 | 2.9 |
| 5 | 3.2 |
| 6 | 3.5 |
| 7 | 3.8 |
| 8 | 4.1 |

TABLE IV-continued

| Solution pH | Partition Coefficient - Ln($a_w/a_o$) |
|---|---|
| 9 | 4.4 |

EXAMPLE 5

Preparation of Kidney Specific Technetium-3-mercaptopropanoic Acid

About 12 milligrams of 3-mercaptopropanoic acid were added to an acetone solution of 99m-TcBr$_6$=(prepared as in Example 4). After 20 minutes reaction time the acetone solution was evaporated to near dryness, diluted to 5 milliliters volume with saline and adjusted to pH 7.4 with 0.5 percent sodium hydroxide. The solution was ready for kidney imaging studies.

The partition coefficient of this technetium complex is shown in the following table:

TABLE V

| Solution pH | Partition Coefficient - Ln($a_w/a_o$) |
|---|---|
| 4 | 2.4 |
| 5 | 2.7 |
| 6 | 3.1 |
| 7 | 3.6 |
| 8 | 4.1 |
| 9 | 4.7 |

EXAMPLE 6

Preparation of Technetium-mercaptosuccinic Acid Complex using Cu II as Catalyst

A solution was prepared containing 50 milligrams of mercaptosuccinic acid in 1.0 ml. of saline, in a 20 ml. pharmaceutical vial. The pH of the solution was approximately 2.

A solution of 30 micrograms of CuSO$_4$5H$_2$O in 10 microliters of saline was added to the vial.

The vial was stoppered, capped and purged with N$_2$.

To prepare the technetium complex of mercaptosuccinic acid, 0.4 millicurie of 99m-TcO$_4$ from a Mo-99-Tc-99m generator was added to the vial in 5 milliliters of saline.

The solution was heated for at least five minutes in a boiling water bath to complete the reaction. Afterwards the solution was neutralized to 7.0–7.4 pH, using 1 molar NaOH solution.

FeCl$_3$ can be used instead of the CuSO$_4$ in this preparation.

Reference has been made herein to thiosaccharides, and these compounds are commonly described in the art as having cyclic structure. They can also exist in tautomeric form as open-chain compounds, and for the purpose of this invention they are to be included within the designation "aliphatic".

What is claimed is:

1. A complex of Tc-99m with a compound of the group consisting of dimercaptosuccinic acid, mercaptosuccinic acid, mercaptoacetic acid, mercaptopropionic acid, 3-mercaptopropylsulfonic acid, thioglucose or thiolactic acid.

2. A complex according to claim 1, in which the complex contains from about 1 to 100 millicuries of Tc-99m for each milligram of complexing agent.

3. A composition comprising an isotonic solution of complexing agent according to claim 1 in a pharmaceutically acceptable parenteral diluent.

4. Composition according to claim 3, in which the parenteral diluent is sterile aqueous isotonic saline solution.

5. A complex according to claim 1, in which the complexing agent is dimercaptosuccinic acid.

6. A complex according to claim 1, in which the complexing agent is thioglucose.

7. A complex according to claim 1, in which the complexing agent is mercaptoacetic acid.

8. A complex according to claim 1, in which the complexing agent is 3-mercaptopropanoic acid.

9. A radiopharmaceutical complex of technetium-99m with a complexing agent selected from the group consisting of mercaptoacetic acid, dimercaptosuccinic acid, mercaptosuccinic acid and mercaptopropionic acid, said complex prepared in the presence of stannous chloride reducing agent.

10. The radiopharmaceutical complex of claim 9 wherein said agent is dimercaptosuccinic acid.

11. A radiopharmaceutical complex of technetium-99m with a complexing agent selected from the group consisting of mercaptoacetic acid, dimercaptosuccinic acid, mercaptosuccinic acid and mercaptopropionic acid, said complex prepared in the presence of a pharmaceutically-acceptable reducing agent for pertechnetate.

12. A radiopharmaceutical complex of reduced technetium-99m with a complexing agent selected from the group consisting of mercaptoacetic acid, dimercaptosuccinic acid and mercaptopropionic acid, wherein the technetium-99m is reduced by stannous chloride.

13. The radiopharmaceutical complex of claim 12 wherein said agent is dimercaptosuccinic acid.

* * * * *

UNITED STATES PATENT AND TRADEMARK OFFICE
CERTIFICATE OF CORRECTION

PATENT NO. : 4,208,398
DATED : Jun. 17, 1980
INVENTOR(S) : David O. Kubiatowicz and Theodore F. Bolles It is certified that error appears in the above—identified patent and that said Letters Patent is hereby corrected as shown below:

Cover Sheet, line "[73] Assignee: Hoffmann-La Roche Inc., Nutley, N.J. "

should be

[73] Assignee: Medi-Physics, Inc., Emeryville, California

Signed and Sealed this

Second Day of September 1980

[SEAL]

Attest:

SIDNEY A. DIAMOND

Attesting Officer

Commissioner of Patents and Trademarks